(12) United States Patent
Tanaka et al.

(10) Patent No.: US 9,816,933 B2
(45) Date of Patent: Nov. 14, 2017

(54) PLASMA SPECTROMETRY METHOD

(71) Applicant: ARKRAY, Inc., Kyoto (JP)

(72) Inventors: Takashige Tanaka, Kyoto (JP);
Yasunori Shiraki, Kyoto (JP);
Akitsugu Kudo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 107 days.

(21) Appl. No.: 14/627,586

(22) Filed: Feb. 20, 2015

(65) Prior Publication Data

US 2015/0241356 A1    Aug. 27, 2015

(30) Foreign Application Priority Data

Feb. 21, 2014  (JP) ................................ 2014-032256
Feb. 19, 2015  (JP) ................................ 2015-030158

(51) Int. Cl.
| | | |
|---|---|---|
| *G01J 3/30* | (2006.01) |
| *G01N 21/68* | (2006.01) |
| *G01N 21/69* | (2006.01) |
| *G01N 21/71* | (2006.01) |
| *G01N 33/48* | (2006.01) |

(52) U.S. Cl.
CPC ............. *G01N 21/68* (2013.01); *G01N 21/69* (2013.01); *G01N 21/71* (2013.01); *G01N 33/48* (2013.01)

(58) Field of Classification Search
CPC ....... G01N 21/714; G01N 21/71; G01N 21/68
USPC ........................................................ 356/316
See application file for complete search history.

(56) References Cited

U.S. PATENT DOCUMENTS

| | | | |
|---|---|---|---|
| 5,825,485 A * | 10/1998 | Cohn ..................... G01N 21/68 333/99 PL |
| 7,875,825 B2 | 1/2011 | Takamura et al. |
| 2007/0164003 A1 | 7/2007 | Takamura et al. |
| 2010/0204926 A1* | 8/2010 | Mettes ................... G01N 27/06 702/25 |
| 2012/0184040 A1* | 7/2012 | Zhang ............... G01N 33/1813 436/80 |
| 2013/0321803 A1 | 12/2013 | Kohara et al. |
| 2015/0015881 A1 | 1/2015 | Ikeda |

FOREIGN PATENT DOCUMENTS

| | | |
|---|---|---|
| EP | 1734360 A1 | 12/2006 |
| EP | 1734360 B1 | 5/2014 |
| EP | 2799846 A1 | 11/2014 |
| JP | 3932368 B2 | 6/2007 |
| JP | 2011-180045 A | 9/2011 |
| JP | 2012-185064 A | 9/2012 |
| WO | 2013/099923 A1 | 7/2013 |

OTHER PUBLICATIONS

Extended European Search Report issued in corresponding European Patent Application No. 15156136.2 dated Jun. 18, 2015.
Kitano et al., "Highly Sensitive Elemental Analysis for Cd and Pb by Liquid Electrode Plasma Atomic Emission Spectrometry with Quartz Glass Chip and Sample Flow," Analytical Chemistry, 83: 9424-9430 (2011).

* cited by examiner

*Primary Examiner* — Sunghee Y Gray
(74) *Attorney, Agent, or Firm* — Morgan, Lewis & Bockius LLP (57) ABSTRACT

A plasma spectrometry method with high reproducibility of plasma light emission is described, wherein the method comprises: a detection step of applying a voltage, thereby detecting the resulting plasma light emission; and non-detection step of detecting no plasma light emission.

19 Claims, 3 Drawing Sheets

PLASMA SPECTROMETRY METHOD

TECHNICAL FIELD

The present invention relates to a plasma spectrometry method.

BACKGROUND ART

As an element analyzer, a plasma generator in which air bubbles are generated in a channel that includes a narrow portion, plasma is generated in the air bubbles, and the resulting light emission in the narrow portion is measured (Patent Literature 1). However, in this device, there is a problem because the reproducibility of the plasma light emission is low.

In order to avoid the retention of the air bubbles that results in a reduction in reproducibility, a method in which a solution is moved in the channel to remove the air bubbles is disclosed (Patent Literature 2). However, in order to move the solution, there are problems in that a discharge unit such as a syringe pump is required, with the result that the size of the plasma generator is increased.

As a method for improving the reproducibility, a method in which a region other than a narrow portion is used as a portion in which the plasma light emission is measured, and the second or subsequent plasma light emissions are measured among multiple times of plasma generation in one voltage application is proposed (Patent Literature 3). However, even by such method, sufficient reproducibility is not obtained.

CITATION LIST

Patent Literatures

Patent Literature 1; Japanese Patent No. 3932368
Patent Literature 2; JP 2011-180045 A
Patent Literature 3; JP 2012-185064 A

SUMMARY OF INVENTION

Technical Problem

The present invention is intended to provide a plasma spectrometry method exhibiting superior reproducibility of plasma light emission, for example.

Solution to Problem

In order to achieve the aforementioned objectives, the plasma spectrometry method of the present invention includes; a detection step of applying a voltage to an electrode system that includes electrodes, thereby detecting plasma light emission generated in a container; and a non-detection step of detecting no plasma light emission, wherein the detection step and the non-detection step are performed repeatedly, and in the detection step, a plasma generation step of generating plasma and a plasma non-generation step of generating no plasma are performed alternately.

Advantageous Effects of Invention

As the results of the studies conducted by the inventors of the present invention, the inventors found that the reproducibility of plasma light emission is associated with air bubbles generated by applying a voltage and can be improved by controlling the generation and the growth of the air bubbles. On the other hand, generally, in the plasma spectrometry method, a detection step of applying a voltage to generate plasma, thereby detecting the resulting plasma light emission and a non-detection step of detecting no plasma light emission are performed repeatedly, where in the detection step, a constant voltage at which the plasma can be generated is continuously applied. As to such a method, the inventors ascertained that in the continuous application of a constant voltage in the detection step, generated air bubbles are grown without any limitation. Therefore, during one detection step, the time when the narrow portion of the channel is isolated and whether plasma is generated by applying the constant voltage cannot be controlled. Accordingly, the plasma light emission becomes unstable. Therefore, the generation and the growth of the air bubbles are controlled not by continuously applying a constant voltage at which plasma can be generated but by alternately performing generation and non-generation of plasma in the detection step, and thus, the reproducibility of the plasma light emission is improved. According to such plasma spectrometry method of the present invention, superior reproducibility of plasma light emission can be achieved, for example. Therefore, the present invention is useful in elemental analysis and the like utilizing plasma generation, for example.

DESCRIPTION OF EMBODIMENTS

As described above, the plasma spectrometry method of the present invention includes: a detection step of applying a voltage to an electrode system that includes electrodes, thereby detecting the resulting plasma light emission generated in a container; and a non-detection step of detecting no plasma light emission, wherein the detection step and the non-detection step are performed repeatedly, and in the detection step, a plasma generation step of generating plasma and a plasma non-generation step of generating no plasma are performed alternately.

The plasma spectrometry method of the present invention is characterized in that the plasma generation step and plasma non-generation step are performed alternately in the detection step, while the other steps and conditions are not particularly limited.

In the detection step of the present invention, "generating plasma" means substantially generating plasma and specifically means generating plasma showing a light emission which can be substantially detected in the detection of plasma light emission, and "generating no plasma" means substantially generating no plasma and specifically means generating no plasma showing a light emission which can be substantially detected in the detection of plasma light emission. In the former case, "generating plasma", can be, for example, specifically referred to as "generating plasma which can be detected by a plasma light emission detector". In the latter case, "generating no plasma" encompasses, for example, "not generating plasma" and "generating plasma at a detection limit or less" and can be, for example, specifically referred to as "being undetectable of plasma light emission by a plasma light emission detector".

The substantial generation and non-generation of plasma can be controlled by a voltage, for example, and those skilled in the art can appropriately set a voltage for generation of plasma showing a light emission which can be substantially detected and a voltage for generation of no plasma.

In the present invention, a repetition of performing the detection step once and the non-detection step once is hereinafter also referred to as "one cycle", and a repetition of performing the plasma generation step once and the plasma non-generation step once in the detection step is hereinafter also referred to as "one set". The detection results of plasma light emission obtained by performing the detection step once or more in one cycle are also referred to as the detection results of plasma light emission in one step (or one sample).

In the detection step of the present invention, by applying a voltage to an electrode system including at least a pair of electrodes, a voltage is applied to a container containing a conductive solution supplied therein, air bubbles are generated in the container, and plasma is generated in the air bubbles, for example.

In the detection step, the plasma generation step of generating plasma and the plasma non-generation step of generating no plasma can be performed by controlling a voltage to be applied. Examples of the control of a voltage to be applied include a method in which an electric circuit is switched between a closed circuit and an open circuit and a method in which an electric circuit is set to a closed circuit, and a voltage value to be applied is changed.

In the former case, for example, by switching an electric circuit between a closed circuit and an open circuit, the plasma generation step and the plasma non-generation step are performed alternately. The state of the closed circuit is the plasma generation step, and by setting an electric circuit to a closed circuit, a voltage at which plasma is generated can be applied. On the other hand, the state of the open circuit is the plasma non-generation step, and by setting an electric circuit to an open circuit, a voltage is not applied, i.e., a voltage can be 0 volt (V). A voltage in the closed circuit is a voltage in the plasma generation step, and a voltage in the open circuit, i.e., 0 V is a voltage in the plasma non-generation step, and plasma is not generated. The voltage in the closed circuit is not particularly limited and can be, for example, a voltage at which plasma is generated, and for example, the lower limit thereof is, 100 V or more, 250 V or more, 600 V or more, or 700 V or more, the upper limit thereof is 1200 V or less, 800 V or less, and the range thereof is from 100 to 1200 V, from 250 to 800 V, from 600 to 800 V, or from 700 to 800 V.

In the latter case, for example, by setting an electric circuit to a closed circuit and alternately applying a relatively high voltage and a relatively low voltage, the plasma generation step and the plasma non-generation step are performed alternately. Such application is hereinafter also referred to as a "pulse application". The relatively high voltage is a voltage at which plasma is generated, and the state where the relatively high voltage is applied is the plasma generation step. On the other hand, the relatively low voltage is a voltage at which plasma is substantially not generated, and the state where the relatively low voltage is applied is the plasma non-generation step. As to the relatively high voltage, the lower limit is, for example, 100 V or more, 250 V or more, 700 V or more, the upper limit is, for example, 1200 V or less, 800 V or less, and the range is, for example, from 100 to 1200 V, from 250 to 800 V, from 700 to 800 V. Any voltage that is lower than the relatively high voltage can be used as the relatively low voltage, and the lower limit is, for example, 0 V or 0 V or more, the upper limit is, for example, less than 100 V, and the range is, for example, 0 V or more to less than 100 V, 0 V.

In the detection step, based on a repetition of performing the plasma generation step once and the plasma non-generation step once as one set, the time of one set is not particularly limited. The time of one set is hereinafter also referred to as the switching (SW) time. As to the SW time, the lower limit is, for example, 1 μs or more, 10 μs or more, the upper limit is, for example, 1000 μs or less, 500 μs or less, 100 μs or less, and the range is, for example, from 1 to 1000 μs, from 1 to 500 μs, from 10 to 100 μs.

In the detection step, based on a repetition of performing the plasma generation step once and the plasma non-generation step once as one set, the proportion of the time of the plasma generation step in the time of one set is not particularly limited. The proportion is hereinafter also referred to as the Duty. As to the Duty, the lower limit is, for example, 1% or more, 10% or more, the upper limit is, for example, less than 100%, 80% or less, 70% or less, and the range is, for example, from 1% or more to less than 100%, from 1% to 80%, from 10% to 70%.

In the detection step, the number of repetitions of performing the plasma generation step and the plasma non-generation step is not particularly limited.

The conditions under which the detection step is performed once in one cycle are described below as an example. The present invention, however, is not limited thereby.

SW time: from 1 to 100 μs

Duty: from 1% to less than 100%

Voltage in the plasma generation step: from 100 to 1200 V

Voltage in the plasma non-generation step: from 0 to 100 V

The application of a voltage to the electrode system can be performed by a voltage application unit. The voltage application unit is not particularly limited, and any unit that can apply a voltage between electrodes can be used, and as a known voltage application unit, a voltage generator or the like can be used, for example. A current between the electrodes to be set can be, for example, from 0.1 to 1000 mA, from 2 to 100 mA.

The generated plasma light emission may be detected continuously or discontinuously in the detection step, for example. In the latter case, for example, in one detection step in one cycle, detections at the start time and the end time may be performed, or detections at intervals may be performed. In the present invention, regardless of the continuous detection or discontinuous detection of plasma light emission, for example, a total of continuous or discontinuous detection results obtained in one detection step based on one detection step in one cycle as one sample (one unit) is regarded as a detection result of one sample. The method for detecting light emission is not particularly limited, and for example, a charge-coupled device (CCD) or the like can be utilized.

The non-detection step is, as mentioned above, a step of detecting no plasma light emission, specifically a step of generating no plasma and detecting no plasma light emission. By performing the non-detection step of generating no plasma after the detection step, for example, air bubbles and plasma generated in the detection step performed immediately before the non-detection step can be disappeared. Therefore, in the detection step of the next cycle, new air bubbles and plasma can be generated.

In the non-detection step, "generating no plasma" means substantially generating no plasma and specifically means generating no plasma showing a light emission which can be substantially detected as mentioned above. In the non-detection step, for example, non-generation of plasma can be controlled by a voltage, and for example, an electric circuit may be set to a open circuit, and the voltage may be set to 0 V, and alternatively, an electric circuit may be set to an closed circuit, and the voltage is set to a voltage at which plasma is not substantially generated. The voltage at which plasma is not substantially generated is, for example, as described above.

In the plasma spectrometry method of the present invention, as described above, the detection step and the non-detection step are performed repeatedly. A repetition of performing the detection step once and the non-detection step ones is also referred so as "one cycle" as mentioned above. In the plasma spectrometry method of the present invention, the number of cycles of performing the detection step and the non-detection step is not particularly limited.

Figure 1:
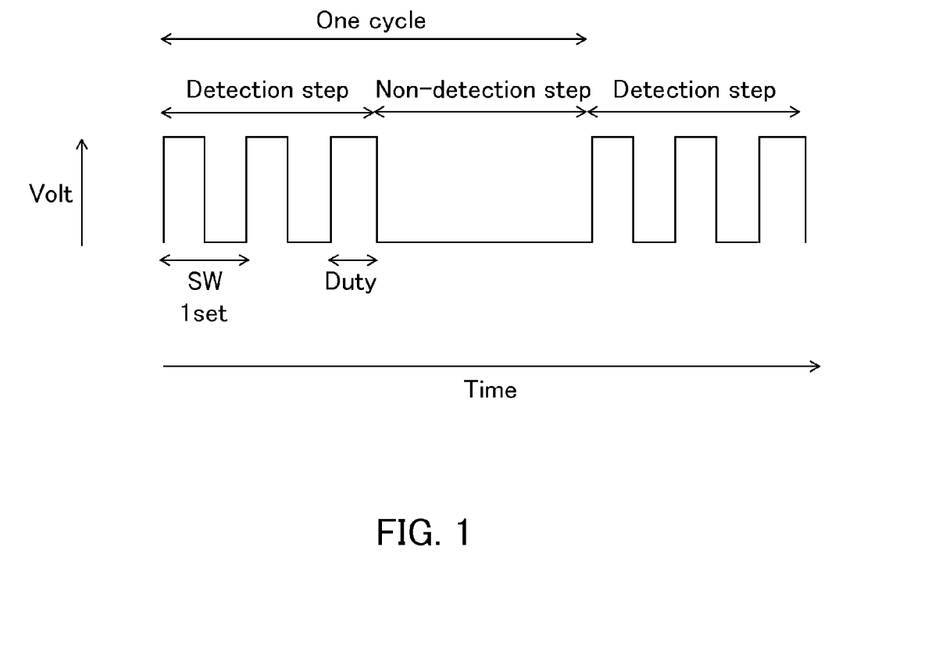
FIG. 1 is a schematic view showing the relationship between the detection step and the non-detection step in the plasma spectrometry method of the present invention.

FIG. 1 schematically shows a repetition of the detection step and the non-detection step in the plasma spectrometry method of the present invention. FIG. 1 is a schematic view and, the number of the detection steps and the non-detection steps, the number of sets in the detection step, a voltage (V), the SW time, the Duty (%), and the like are not at all limited thereby.

In the plasma spectrometry method of the present invention, the conductive solution may contain a sample, for example. The sample is, for example, a specimen. The sample may be a liquid sample or a solid sample. Examples of the sample include a sample derived from a biological body, a sample derived from the environment, a metal, a chemical substance, and a pharmaceutical. The sample derived from a biological body is not particularly limited, and examples thereof include urine, blood, hair, and an umbilical cord. Examples of the blood sample include erythrocytes, whole blood, serum, and plasma. Examples of the biological body include humans, nonhuman animals, and plants. Examples of nonhuman animals include mammals except for humans, and fish and seafood. A sample derived from the environment is not particularly limited, and examples thereof include food, water, the ground, the atmosphere, and air. Examples of metals include heavy metals such as Bi (bismuth), Hg (mercury), Cd (cadmium), Pd (palladium), Zn (zinc), Tl (thallium), Ag (silver), Pb (lead), and the like. Examples of chemical substance include reagents, pesticides, and cosmetics. Examples of food include fresh food and processed food and the like. Examples of water include drinking water, ground water, river water, seawater, and domestic wastewater.

In the case where a subject to be analyzed is a metal, the sample may contain a reagent for separating a metal in the sample, for example. The reagent can be, for example, a chelating reagent, an acid, or an alkali, and specific examples thereof include dithizone, thiopronine, meso-2,3-dimercapto succinic acid (DMSA), sodium hydroxide, lithium hydroxide, 1,2-dimercapto-1-propanesulfonic acid sodium salt (DMPS), nitric acid, succinic acid, glycine, cysteine, and the like.

The sample may contain an electrolyte for imparting conductivity. Examples of the electrolyte include nitric acid, acetic acid, hydrochloric acid, potassium chloride, sodium chloride, and a buffer solution, and among them, nitride acid is preferable because the influence on the analysis can be sufficiently avoided.

The concentration of the electrolyte in the sample is not particularly limited.

In the plasma spectrometry method of the present invention, the container is not particularly limited and can be any container that can be filled with the conductive solution and preserves the conductive solution. Examples of the container include containers in a closed-end cylindrical shape, a cup shape, and the like and a chip having a channel. It is preferred that in the plasma spectrometry method of the present invention, the conductive solution is, for example, supplied to the container, and the electrode system is arranged so as to sandwich the detection portion that detects the plasma light emission in the container. In the detection step, a region to be detected in the container is not particularly limited.

In the case where the container is a chip having a channel, it is preferred that a voltage is applied to the channel, and plasma light emission generated in the channel is detected.

A chip having a channel is shown below as an example of the container. The present invention, however, is not limited thereby.

It is preferred that, in the chip, the channel has, for example, a first region, a narrow portion, and a second region, and the narrow portion is in communication with the first region and the second region and has a cross-sectional area smaller than the first region and the second region. Each of the first region, the narrow portion, and the second region has a void (hollow), so that the inside of them are in communication with one another in this order. In the chip, the direction from the first region toward the second region is referred to as the "longitudinal direction", the "axis direction", or the "electric field direction", and with a central focus on the narrow portion, the first region side is referred to as the upstream side, and the second region side is referred to as the downstream side. The direction that is perpendicular to the longitudinal direction and is the plane direction is referred to as the "width direction", and the direction that is perpendicular to the longitudinal direction and is the vertical direction of the chip is referred to as the "height direction" or the "depth direction". The distance in the longitudinal direction is referred to as the "length", the distance in the width direction is referred to as the "width", and the distance in the height direction is referred to as the "height. The "cross-sectional area" in the channel means a cross-sectional area of the void inside the channel in the width direction (the direction perpendicular to the longitudinal direction), unless otherwise shown.

It is preferred that a voltage is applied to the narrow portion of the chip in the detection step, for example. The detection portion in the chip is not particularly limited, and in the detection step, for example, plasma light emission generated in the narrow portion or a portion other than the narrow portion may be detected. The detection portion is, for example, preferably only the narrow portion with the center of the narrow portion as the central point, and preferably only a region other than the narrow portion with a point other than the center of the narrow portion as the central point.

The shape of the channel is not particularly limited, and examples of the shape of the cross section of the channel include: a circular shape such as circle, an exact circle, or an ellipse; a semicircular shape; and a polygonal shape such as a triangle, a quadrangle, a square, a rectangle, or the like. In the channel, the first region, the narrow region, and the second region may have different cross-sectional shapes, for example.

In the chip, the narrow portion is a region having a cross-sectional area smaller than the first region and the second region and is preferably a region having a cross-sectional area significantly smaller than the first region and the second region. It is preferred that the narrow portion is specifically a region with a central focus on a portion having the smallest cross-sectional area in the channel. It is preferred that the narrow portion has an almost constant cross-sectional area over the full length thereof, for example. "The narrow portion having an almost constant cross-sectional area" also encompasses the meaning of a region having a cross-sectional area gradually increased toward the upstream side and the downstream side in the longitudinal direction with a central focus on a portion having the smallest cross-sectional area in addition to the meaning of a region having a completely constant cross-sectional area, for example. The cross-sectional area may be successively or non-successively increased, for example. In this case, the narrow portion is a successive region having cross-sectional areas of 50,000 times or less, 1000 times or less, 500 times or less, and 100 times or less relative to the smallest cross-sectional area, for example.

The cross-sectional area of the narrow portion may be set by narrowing the width, reducing the height, or both of them, relative to the first region and the second region.

In the chip, the shape of the first region is not particularly limited and can be any shape of a region having a cross-sectional area larger than the narrow portion. The first region may have an almost constant cross-sectional area or a different cross-sectional area over the full length thereof, for example.

In the former case, "a region having an almost constant cross-sectional area" encompasses the meaning of a region having a cross-sectional area gradually increased from the end on the downstream side (end on the narrow portion side) toward the end on the upstream side in the longitudinal direction in addition to the meaning of a region having a completely constant cross-sectional area, for example. The cross-sectional area may be successively or non-successively increased, for example. In this case, the first region is a successive region having cross sectional areas of 50,000 times or less, 1000 times or less, and 500 times or less relative to an average cross-sectional area over the full length as 1, for example. In this case, for example, it can be said that, in the interface between the narrow portion and the first region in the channel, the cross-sectional area changes at an angle of about 90° to at least one of the longitudinal direction, width direction, and height direction.

In the latter case, the first region can be in a form in which the cross-sectional area is successively or non-successively increased from the end on the downstream side to the end on the upstream side in the longitudinal direction, for example, i.e., a form in which the cross-sectional area is gradually increased over the full length. The change in cross-sectional area may be set by the change in width, height, or both of them, for example. In this case, the first region may be in a form having a tapered portion in which one or both of the width and the height is enlarged from the end on the downstream side toward the end on the upstream side so as to have a tapered shape. In the latter case, for example, the first region can be in a form in which the cross-sectional area is successively or non-successively increased from the end on the downstream side to the predetermined portion on the upstream side and is constant from the predetermined portion to the end on the upstream side in the longitudinal direction. The change in cross-sectional area may be set by the change in width or height, for example. In this case, the first region may be in a form having a tapered portion in which one or both of the width and the height is enlarged from the end on the downstream side toward the predetermined portion so as to have a tapered shape and a non-tapered portion in which one or both of the width and the height is constant from the predetermined portion to the end on the upstream side.

In the case where the first region has a tapered portion in which the height is tapered from the downstream side toward the upstream side, the flare angle in the tapered portion is, for example, from 10° to 90°, from 10° to 80° to the longitudinal direction. Moreover, in the case where the first region has a tapered portion in which the width is tapered from the downstream side towered the upstream side, the flare angle in the tapered portion is, for example, from 10° to 90°, from 10° to 80° to the longitudinal direction.

In the chip, the shape of the second region is not particularly limited and may be any shape having a cross-sectional area larger than the narrow portion. The second region can be described with reference to the description of the first region by reading the "first region" as the "second region", "upstream" as "downstream", and "downstream" as "upstream", for example. The shapes of the first region and the second region may be symmetrical to each other and under the same conditions or different conditions or may be asymmetrical to each other.

The cross-sectional areas of the first region and the second region are, for example, more than 1×, 3× or more, 10× or more, 30× or more, 100× or more relative to the smallest cross-sectional area in the narrow portion. The upper limit thereof is not particularly limited and is, for example, 10,000 times or less, 8000 times or less, or 5000 times or less.

As to the first region and the second region in the chip, the width is, for example, from 2 μm to 30 mm, from 300 μm to 5 mm, or from 500 μm to 1 mm, and the height is, for example, from 0.5 μm to 1 mm, from 10 to 300 μm, or from 50 to 200 μm.

As to the narrow portion in the chip, the width is, for example, from 0.5 μm to 1 mm, from 10 to 300 μm, or from 50 to 200 μm, and the height is, for example, from 0.5 μm to 1 mm, from 10 to 300 μm, or from 50 to 200 μm.

The chip may include an electrode, or a device in which the chip is set may include an electrode, for example. The chip may be any chip in which electrodes, i.e., a cathode and an anode are arranged so that the detection portion (for example, the narrow portion or a portion other than the narrow portion) is positioned between the cathode and the anode in use. The electrode is not particularly limited and can be, for example, a solid electrode, and can be a bar electrode or the like as a specific example.

The material of the electrode is not particularly limited and may be a solid conductive material, and examples thereof include platinum, gold, carbon, zinc, brass, copper, stainless steel, iron, and the like. The cathode is, for example, preferably carbon, and the anode is, for example, preferably carbon.

The chip preferably further includes a first reservoir and a second reservoir, for preserving a conductive solution. In this case, for example, one end of the first region is in communication with the narrow portion, the other end of the first region is in communication with the first reservoir, one end of the second region is in communication with the narrow portion, and the other end of the second region is in communication with the second reservoir. The cathode may be arranged in the first reservoir, for example, and the anode may be arranged in the second reservoir, for example.

The shape and the size of each of the first reservoir and the second reservoir are not particularly limited and may be any shape in which a conductive solution can be preserved. The shape of each of the first reservoir and the second reservoir is not particularly limited, and examples thereof include a polygonal prism shape such as a triangular prism or a quadrangular prism and a cylindrical shape such as an exact cylinder or an elliptic cylinder, and a conical shape.

The material of the chip is not particularly limited, and for example, it is preferred that the inner wall of the chip except the electrode is formed of an insulating material, and it is more preferred that the entire chip except the electrode is formed of an insulating material. A method for producing the chip is not particularly limited, and for example, a molded article having a channel and the like may be produced by injection molding or the like, or a channel and the like may be formed in a base material such as a plate. A method for forming the channel and the like is not particularly limited, and examples thereof include lithography and cutting.

The insulating material is not particularly limited, and examples thereof include a resin, silicone, glass, paper, ceramics, and rubber. Examples of the resin include thermoplastic resins such as polyethylene, polypropylene, polystyrene, polyvinyl chloride, polyethylene terephthalate, polymethacrylate, polyamide, a saturated polyester resin, an acrylic resin, polybutylene terephthalate (PBT), polyether ether ketone (PEEK), and polymethylpentene (for example, TPX®), epoxy resins such as an urea resin, a malemine resin, a phenol resin, a fluorine resin, and glass epoxy, and a thermosetting resin such as an unsaturated polyester resin. The silicone can be, for example, polydimethylsiloxane.

In the present invention, as mentioned above, the generation and the non-generation of plasma can be controlled by a voltage, for example, and those skilled in the art can appropriately set the conditions of the voltage. In the case where the container is a chip having the narrow portion, for example, the conditions of a voltage at which plasma is generated and a voltage at which plasma is not generated are preferably as mentioned above, for example.

For example, in the case where the container has no narrow portion, specifically, for example, in the case where the container is a closed-end cylindrical-shaped container, the conditions of the voltages are as follows. As to the voltage at which plasma is generated, the lower limit is, for example, 10 V or more, or 200 V or more, and the upper limit is, for example, 1200 V or less, or 500 V or less. As to the voltage at which plasma is not generated, the lower limit is 0 V or 0 V or more, and the upper limit is, for example, less than 10 V, or 1.5 V or less.

Examples of the present invention are described below. The present invention, however, is not limited thereby.

EXAMPLES

Example 1

The reproducibility of plasma light emission was checked using a chip having a narrow portion.

(1) Chip for Plasma Generation

Figure 2A:
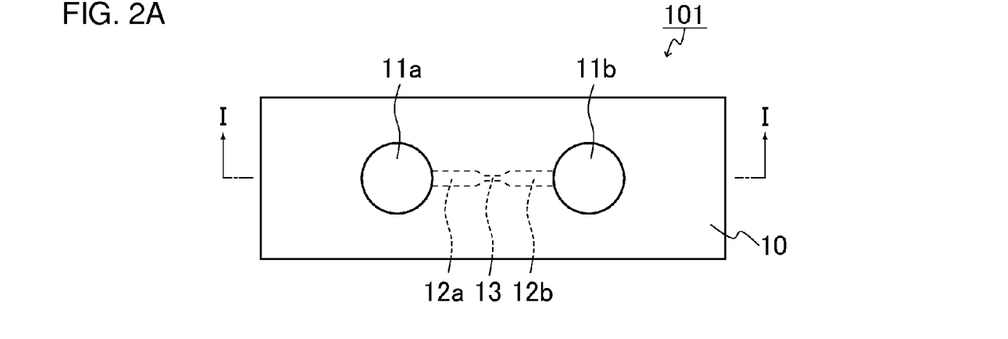
FIGS. 2A to 2E are schematic views of a chip of Example 1 in the present invention.
Figure 2B:
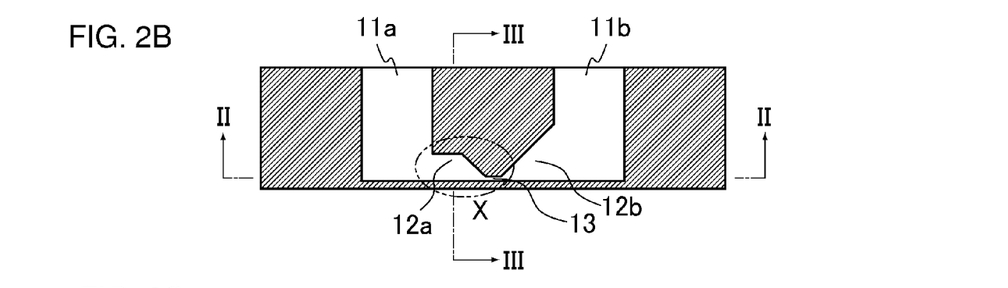
Figure 2C:
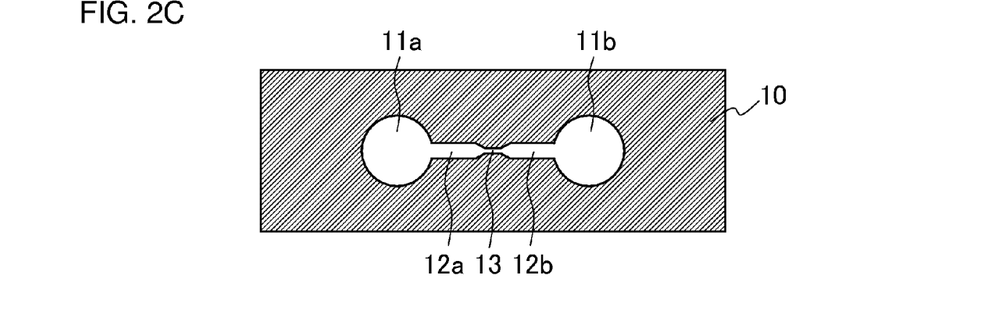
Figure 2D:
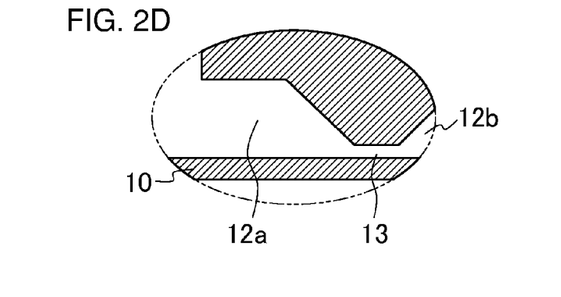
Figure 2E:
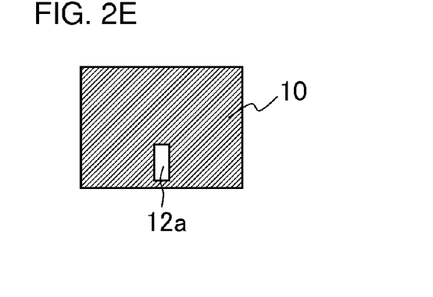

A chip 101 for plasma generation shown in FIGS. 2A to 2E was produced. FIG. 2A is a top view of the chip 101, FIG. 2B is a cross-sectional view in the I-I direction of FIG. 2A, FIG. 2C is a cross-sectional view in the II-II direction of FIG. 2B, FIG. 2D is an enlarged view of a region (X) indicated by dashed lines of FIG. 2B, and FIG. 2E is a cross-sectional view in the III-III direction of FIG. 2B. Specifically, a plate of quartz glass as a lower substrate and a plate of polybutylene terephthalate (PBT, DURANEX® 2002, manufactured by Polyplastic) as an upper surface were provided. A void shown in FIGS. 2A to 2E was formed in the upper substrate. The upper substrate and the lower substrate were then joined to each other with a ultraviolet curable adhesive. Thus, the chip 101 for plasma generation in which a narrow portion 13 was formed in a substrate 10 composed of the upper substrate and the lower substrate was produced.

The size of each portion of the chip 101 for plasma generation was set as follows.

Narrow portion 13
  Length: 600 μm
  Width: 220 μm
  Height: 30 μm
First region 12a
  Full length: 2.5 mm
  Width: 1 mm
  Angle of tapered region: 45°
Second region 12b
  Length: 2.5 mm
  Width: 1 mm
  Angle of tapered portion: 45°
First reservoir 11a and second reservoir 11b
  Diameter: 3.2 mm
  Height: 6 mm
Chip 101
  Full length: 35 mm
  Full width: 12 mm
  Height: 6 mm (2) Measurement of Plasma Light Emission Thiopronine was dissolved in nitric acid so as to have a final concentration of 500 mmol/L. Thus, a thiopronine sample was prepared. This was used as a conductive solution.

In the chip 101 for plasma generation, a cathode was inserted into a first reservoir 11a, and an anode was inserted into a second reservoir 11b. As the cathode and the anode, carbon electrode bars (DPP CRP microcarbon rod, diameter: 0.28 mm, manufactured by Sano Factory) were used. Subsequently, in the chip 101 for plasma generation, 80 μL of the conductive solution was introduced into the first reservoir 11a and was led out to the second reservoir 11b. Thus, the conductive solution was introduced into the first region 12a, the narrow portion 13, and the second region 12b.

A pulse voltage was then applied between the cathode and the anode, and plasma light emission in the narrow portion of the chip 101 for plasma generation was analyzed (n=7). The conditions under which a voltage was applied (hereinafter referred to as the application conditions) and the conditions under which plasma light emission was analyzed (hereinafter referred to as the analysis conditions) were as follows. The coefficient of variation (C.V.) value was determined from each of the count values of the first cycle to the twentieth cycle and the count values of the twenty-first cycle to the fortieth cycle.

(Application Condition)
Applied voltage: Repetition of 750 V and 0 V
Applied current: 750 mA
SW time: 50 μs
Duty: 16%
Time in one detection step: 350 ms
The number of sets: 7 sets
The number of cycles: 40 cycles
(Analysis Conditions)
Analysis region: a region having a diameter of 400 μm with the center of the narrow portion as the central point
Optical fiber: a single core having a diameter of 400 μm As a comparative example, a light emission spectrum was analyzed in the same manner as described above using the same chip except that not a pulse voltage, but a continuous voltage (750 V) was applied during the detection step.

Figure 3:
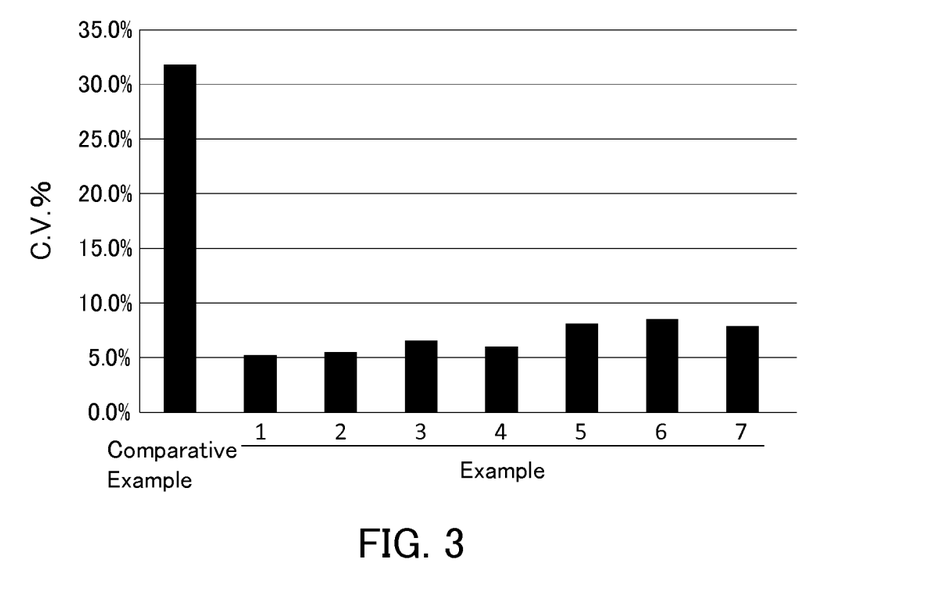
FIG. 3 is a graph showing the coefficient of variation (C.V.) values of the count values of plasma light emission in Example 1 of the present invention.

The results are shown in FIG. 3. FIG. 3 is a graph showing the count values of plasma light emission and shows the C.V. values of the twenty-first cycle to the fortieth cycle. In FIG. 3, the vertical axis shows the C.V. value.

As shown in FIG. 3, the example in which a pulse voltage was applied in the detection step showed lower C.V. values than the comparative example in which a continuous voltage was applied, and the C.V. values of the example were not changed. Accordingly, it was found that high reproducibility of plasma light emission could be achieved by applying a pulse voltage in the detection step.

Example 2

The reproducibility of plasma light emission was checked using a cup-shaped container.

A closed-end cylindrical-shaped transparent container made of PMMA (the height 15 mm×the diameter Φ10 mm) was provided. Quartz glass was arranged in the center of the bottom part of the container. An anode and a cathode were arranged in the container. The cathode was arranged in the axis direction of the container, and the tip of the cathode was in contact with the quartz glass in the bottom part of the container. As the cathode, a brass bar with a diameter of 0.2 mm in which a region from the tip to the 0.3 mm was exposed, and the other region was insulated was used. The anode was arranged in the direction perpendicular to the axis direction from the side surface of the container toward the inside. As the anode, a carbon electrode bar with a diameter of 3 mm was used. Then, a light emission spectrum of plasma light emission was analyzed (n=2) except that the conductive solution of Example 1 was introduced into the container, and a pulse voltage was applied under the following conditions.

(Application Condition)
Applied voltage: Repetition of 280 V and 0V
SW time: 100 μs
Duty: 80%
The number of cycles: 80 cycles As a comparative example, a light emission spectrum was analyzed in the same manner as described above using the same container except that not a pulse voltage but a continuous voltage (750 V) was applied during the detection step.

Figure 4:
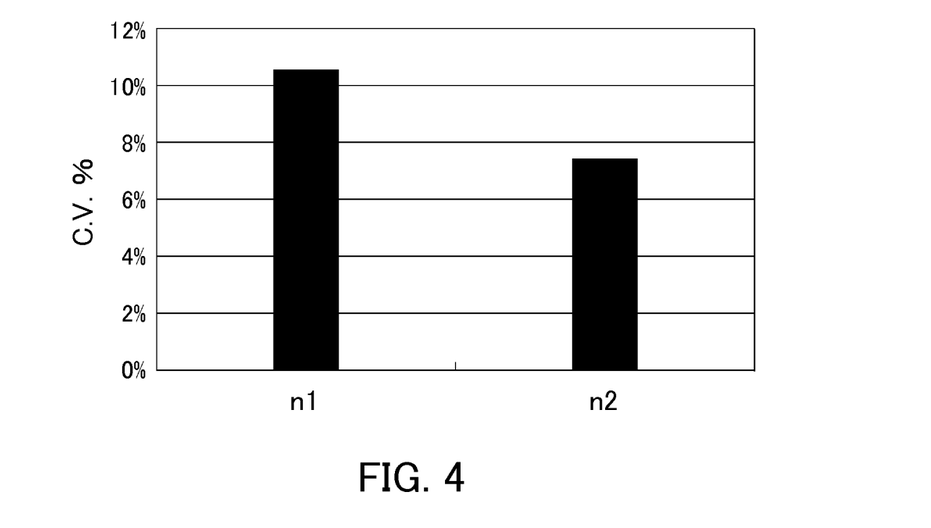
FIG. 4 is a graph showing the C.V. values of the count values of plasma light emission in Example 2 of the present invention.

The results are shown in FIG. 4. FIG. 4 is a graph showing the count values of plasma light emission in the example and shows the C.V. values of the first cycle to eightieth cycle. In FIG. 4, the vertical axis indicates the C.V. value, and the analyses were represented by n1 and n2.

In the comparative example, generation of plasma was not found, and a light emission spectrum itself could not be detected. In contrast, in the example in which a pulse voltage was applied, as shown in FIG. 4, the C.V. values were low and the changes were not found. Accordingly, it was found that high reproducibility of plasma light emission could be achieved by applying a pulse voltage in the detection step.

While the invention has been particularly shown and described with reference to exemplary embodiments and examples thereof, the invention is not limited to these embodiments and examples. It will be understood by those of ordinary skill in the art that various changes in form and details may be made therein without departing from the spirit and scope of the present invention as defined by the claims.

This application claims priority from Japanese Patent Application No. 2014-32256 filed on Feb. 21, 2014, the entire subject matter of which is incorporated herein by reference.

INDUSTRIAL APPLICABILITY

According to the plasma spectrometry method of the present invention, superior reproducibility of plasma light emission can be achieved. Therefore, the present invention is useful in element analysis utilizing plasma generation.

The invention claimed is:
1. A plasma spectrometry method comprising:
a detection step of applying a voltage to an electrode system comprising electrodes, and detecting the resulting plasma light emission generated from a target sample in a container containing a conductive solution of the target sample; and
a non-detection step of detecting no plasma light emission,
wherein
the detection step and the non-detection step are performed repeatedly, and
in the detection step, a step of generating plasma and a step of generating no plasma are performed alternately, resulting in controlled generation and growth of air bubbles in the conductive solution which improves reproducibility of the plasma light emission.
2. The plasma spectrometry method according to claim 1, wherein
the plasma generation step and the plasma non-generation step are performed alternately by switching an electric circuit between a closed circuit and an open circuit.
3. The plasma spectrometry method according to claim 1, wherein
a voltage in the plasma generation step is 100 V or more.
4. The plasma spectrometry method according to claim 1, wherein
the plasma generation step and the plasma non-generation step are performed alternately by setting an electric circuit to a closed circuit and alternately applying a high voltage and a low voltage.
5. The plasma spectrometry method according to claim 4, wherein
a voltage in the plasma generation step is 100 V or more.
6. The plasma spectrometry method according to claim 5, wherein
a voltage in the plasma non-generation step is less than 100 V.

7. The plasma spectrometry method according to claim 1, wherein
based on a repetition of performing the plasma generation step once and the plasma non-generation step once as one set, the time for completing one set is from 1 to 1000 μs.

8. The plasma spectrometry method according to claim 1, wherein
based on a repetition of performing the plasma generation step once and the plasma non-generation step once as one set, the time associated with the plasma generation step compared to the time for completing one set is from 1% or more to less than 100%.

9. The plasma spectrometry method according to claim 1, wherein
the light emission is detected continuously or discontinuously.

10. The plasma spectrometry method according to claim 1, wherein
the container is a chip comprising a channel, and
a voltage is applied to the channel, and the resulting plasma light emission generated in the channel is detected.

11. The plasma spectrometry method according to claim 10, wherein
the channel has a first region, a narrow portion, and a second region, and
the narrow portion is in communication with the first region and the second region and has a cross-sectional area smaller than the first region and the second region.

12. The plasma spectrometry method according to claim 11, wherein
at least a pair of electrodes is arranged so as to sandwich the narrow portion.

13. The plasma spectrometry method according to claim 11, wherein
a voltage is applied to the narrow portion.

14. The plasma spectrometry method according to claim 13, wherein
at least a pair of electrodes is arranged so as to sandwich the narrow portion.

15. The plasma spectrometry method according to claim 11, wherein
the plasma light emission generated in the narrow portion or a portion other than the narrow portion is detected.

16. The plasma spectrometry method according to claim 15, wherein
at least a pair of electrodes is arranged so as to sandwich the narrow portion.

17. The plasma spectrometry method according to claim 1, wherein
the container is filled with a conductive solution, and
the conductive solution contains a sample.

18. The plasma spectrometry method according to claim 17, wherein
the sample is derived from a biological body.

19. The plasma spectrometry method according to claim 18, wherein
the sample derived from a biological body is urine.

* * * * *